United States Patent [19]

Krongauz et al.

[11] Patent Number: 5,322,945

[45] Date of Patent: Jun. 21, 1994

[54] PHOTOCHROMIC SPIROOXAZINE MONOMERS AND POLYSILOXANES

[75] Inventors: Valeri Krongauz, Rehovot; Frida Buchhultz, Rishon Lezion; Alexander Zelichenok, Rehovot, all of Israel; Shlomo Yitzchaik, Evanston, Ill.

[73] Assignee: Yeda Research and Development Co. Ltd., Rehovot, Israel

[21] Appl. No.: 19,765

[22] Filed: Feb. 19, 1993

[51] Int. Cl.$^5$ ............................ C07F 7/08; C07F 7/10; C07F 7/18

[52] U.S. Cl. ........................................ 544/69; 544/71; 252/586; 351/163; 430/345; 359/241; 359/642

[58] Field of Search .................... 544/69, 71; 252/586; 351/163; 350/409, 354; 430/345

[56] References Cited

PUBLICATIONS

J. Crano et al., in *Applied Photochromic Polymer Systems*, pp. 31–76 (C. B. McArdle, Editor, Blackie & Son, Glascow/London) (1992).
E. Goldburt et al., *Macromolecules*, 17:1225–1230 (1984).
I. Cabrera et al., *Macromolecules*, 20:2713–2717 (1987).
I. Cabrera et al., *Angew. Chem.*, 26:1178–1180 (1987).
S. Yitzchaik et al., *Macromolecules*, 23:707–713 (1990).
S. Yitzchaik et al., *Liq. Crystals*, 8:677–686 (1990).
L. Shragina et al., *Liq. Crystals*, 7:643–655 (1990).
T. Bercovici et al., *J. Phys. Chem.*, 80:108–111 (1976).
E. Goldburt, et al., *Macromolecules*, 17:1876–1878 (1984).
H. Eckhart et al., *Polymer*, 28:1959–1964 (1987).

*Primary Examiner*—Paul F. Shaver
*Attorney, Agent, or Firm*—Reising, Ethington, Barnard, Perry & Milton

[57] ABSTRACT

A method of making a photochromic polysiloxane includes the steps of forming a photochromic spironaphthooxazine monomer including an alkene terminated side and, by addition reaction, covalently bonding the alkene carbon to [SiH] moieties of a siloxane polymer. Novel spironaphthooxazine monomers and photochromic polysiloxanes are disclosed.

12 Claims, 5 Drawing Sheets

PHOTOCHROMIC SPIROOXAZINE MONOMERS AND POLYSILOXANES

TECHNICAL FIELD

The present invention relates to photochromic compounds and specifically to photochromic polysiloxanes which can be used as coatings for lens surfaces and the like to provide light-sensitive darkening effects.

BACKGROUND OF THE INVENTION

Photochromic polymers, that is, polymers which contain photochromic groups in a macromolecule, are materials of significant technological potential in many industrial fields. For example, such polymers can be used in the manufacture of the plastic material of eye lenses and the manufacture of windows for the automobile industry.

Spirooxazines and their use in photochromic lenses have been recently reviewed by Crano et al.[1] There has also been a significant amount of research reported on a number of side-chain photochromic polymers in which photochromic spiropyran or spirooxazine side groups are attached to a main chain through a flexible spacer[2-6]. The structure of these compounds allows incorporation of a very high content of a photochrome in a polymer which can reach 100%. That is, each structural unit of the polymer contains the photochromic group. Properties of such polymers can be substantially different from the properties of the polymers containing photochromic molecules as solute, as photochromic compounds have been usually employed in photochromic lenses. Such solutions in polymers have inherent restrictions in solubility of the photochromic compound.

Liquid crystalline polyacrylates and polysiloxanes containing different photochromic spironaphthooxazine side groups were recently reported[6]. A two-step reaction was described therein for the synthesis of the liquid crystalline polysiloxane polymers containing spiroindolinenaphthooxazine side groups. First, the siloxane polymer was reacted with a mixture of a mesogen, such as p-cyanophenylbenzoate, and an active ester that contains an olefinic terminal group. Then the spironaphthooxazine photochromic groups was incorporated into the active ester-mesogen copolymer by reaction of the copolymer with 5-amino-spiroindoline-naphthooxazine, resulting in photochromic liquid crystal polysiloxanes comprising also mesogenic groups.

The aforementioned synthesis was effective but includes several limitations. Most significantly, the reaction of the photochromic monomer with the active ester side groups could not go to completion because several of the ester groups were hydrolyzed to free acid groups, which influence the photochrome kinetics thereby slowing the change of color rates.

The present invention provides a variety of new photochromic amorphous polysiloxanes with spironaphthooxazine side groups and a novel single-step synthetic method used for the incorporation of the spirooxazine in the polymer macromolecules. The present invention provides a one-step synthesis which avoids the use of active ester side chain polymers thereby providing a high amount of incorporation of photochromic groups per -Si-H moiety while not having the prior art limitations presented by the active ester groups forming into free acid sites.

SUMMARY OF THE INVENTION

In accordance with the present invention, there is provided a photochromic compound of the formula:

wherein $R^1$ is selected from the group consisting of (A) hydrogen, alkyl, phenyl, benzyl, or an alkyl substituted by halogen, hydroxy, lower alkoxy, carboxyl, or lower alkoxycarbonyl, or phenyl or benzyl substituted by cyano or by one or more halogens; and (B)—$(CH_2)_n$—$CH=CH_2$ wherein n is an integer from 1 to 20;

when $R^1$ is (B), then $R^2$ through $R^8$ are each selected from the group consisting of hydrogen, lower alkyl, and lower alkyl including substitutions from the group consisting of halogen, hydroxy, and lower alkoxy;

when $R^1$ is (A), then one of $R^2$ through $R^8$ are (C) —X—$(CH_2)_n$—$CH=CH_2$ wherein n is an integer from 1 to 20 and X is selected from the group consisting of a covalent bond, O, N—R' (wherein R' is H or lower alkyl), CO—O, CO—NH, and —CH=N and the remaining ones of $R^2$ through $R^8$ are selected from the group consisting of a hydrogen, alkyl and alkyl substituted by halogen, hydroxy and lower alkoxy; and $R^9$ and $R^{10}$ form a condensed benzene or pyridine ring.

The present invention further provides a photochromic polysiloxane including the functional moiety and one or both of the functional moiety selected from the group including and wherein R" is a $C_1$ through $C_{15}$ alkyl, R''' is H or $C_4$ through $C_{15}$ alkyl, G is a photochromic radical derived from a compound as defined by the prior formula covalently bonded through the alkene carbon of radical $R^1$ as moiety (B) or of $R^2$ through $R^8$ as moiety (C); and the polysiloxanes being cyclic or linear including terminal groups of the formulas:

(R")₃—Si—O—, covalently bonded to the Si atom of an [Si—O] moiety and Si—(R")₃ covalently bonded to the —O— atom of an [Si—O] moiety.

Further, the present invention provides a method of making a photochromic polysiloxane, the method including the steps of forming a photochromic spironaphthooxazine monomer including an alkene terminated side chain and by addition reaction covalently bonding the alkene carbon to (SiH) moieties of a siloxane polymer.

BRIEF DESCRIPTION OF THE FIGURES

Other advantages of the present invention will be readily appreciated as the same becomes better understood by reference to the following detailed description when considered in connection with the accompanying drawings wherein.

DETAILED DESCRIPTION OF THE INVENTION

The present invention provides a photochromic compound, sometimes referred to as a photochromic monomer, a photochromic polysiloxane including functional moieties having the aforementioned monomer covalently bonded thereto, and a method of making the aforementioned photochromic polysiloxanes polymer. Inherent in each of these embodiments is the concept of a photochromic compound including a side chain (commonly referred to as a linker arm or spacer) including an alkene functionality.

The photochromic compounds or monomers of the present invention have the general formula:

wherein $R^1$ is selected from the group consisting of (A) hydrogen, alkyl, phenyl, benzyl, or an alkyl substituted by halogen, hydroxy, lower alkoxy, carboxyl, or lower alkoxycarbonyl, or phenyl or benzyl substituted by cyano or by one or more halogens; and (B) —(CH₂)ₙ—CH=CH₂ wherein n is an integer from 1 to 20;

when $R^1$ is (B), then $R^2$ through $R^8$ are each selected from the group consisting of hydrogen, lower alkyl, and lower alkyl including substitutions from the group consisting of halogen, hydroxy, and lower alkoxy;

when $R^1$ is (A), then one of $R^2$ through $R^8$ are (C) —X—(CH₂)ₙ—CH=CH₂ wherein n is an integer from 1 to 20 and X is selected from the group consisting of a covalent bond, O, N—R' (wherein R' is H or lower alkyl), CO—O, CO—NH, and —CH=N and the remaining ones of $R^2$ through $R^8$ are selected from the group consisting of a hydrogen, alkyl and alkyl substituted by halogen, hydroxy and lower alkoxy; and $R^9$ and $R^{10}$ form a condensed benzene or pyridine ring.

The above-described monomer is characterized by including a linker arm selected from (B) —(CH₂)ₙ—CH=CH₂ extending from the indoline nitrogen as the $R^1$ group, and (C) —X— (CH₂)ₙ—CH=CH₂ when the linker arm extends from a phenyl carbon as in groups $R^4$ and $R^5$ or an indoline carbon as in groups $R^2$ and $R^3$.

The chemical differences between these two groups are due to the nature of the synthetic reactions used to assemble the photochromic compound as discussed below. In either case, an alkene linker arm extends from either the indole nitrogen or carbon or a phenyl carbon, the linker arm having a length of 3 to 22 carbons.

The number of carbons in the linker arm is significant with regard to the efficiency of the addition reaction to the polymer as demonstrated in the experimental section below. That is, it has been found that by increasing the length of the linker arm, the efficiency of the addition reaction is increased.

Each photochromic monomer includes a single linker arm as groups $R^1$ through $R^8$, the remaining groups being various functionalities as defined above. As discussed below, these functionalities can be synthesized by chemical reactions known in the art, once one understands the present invention.

Preferred compounds of the present invention are:

wherein $R^1$, $R^2$ and $R^3$ are preferably methyl, X is preferably —O— and n is preferably an integer of 1 through 8, most preferably 1 or 4.

The photochromic compounds or monomers discussed above can be made by two distinct types of reactions, depending upon whether the linker arm is bound to the indole nitrogen or to an indole or phenyl carbon.

Spiroindolinenaphthooxazine monomers wherein the linker arm extends from the indole nitrogen are made by first forming an indoline derivative having a methylene side chain extending therefrom at position 2 (a so-called "Fischer base") and then forming the spiroindolinenaphthooxazine by a thermal condensation reaction with an orthohydroxynitroso aromatic derivative according to the equation[1]:

Substituting 1-nitroso-2-naphthol by 5-nitroso-6-hydroxy-quinoline, the spiro[indoline-2,3'-[3H]pyrido[3,2-f]-[1,4]benzoxazine] derivatives are obtained, i.e., the compounds wherein $R^9$ and $R^{10}$ form a condensed pyridine ring. Synthesis of different spiroindolinenaphthooxazine and spiroindolinepyridobenzoxazines were described by Crano et al.[1], and in the patents cited therein U.S. Pat. No. 4,215,010 (Hovey et al., 1980), German Offen. 1,927,849 (Arnold and Vollmer, 1970), U.K. 1,186,987 (Ono and Osada, 1970), U.S. Pat. No. 4,637,698 (Kwak and Hurditch, 1987), U.S. Pat. No. 4,816,584 (Kwak and Chen, 1989), U.S. Pat. No. 4,831,142 (Kwak, 1989) all of them herein incorporated by reference.

The indoline derivative (the Fischer base) is prepared by reacting a suitable indolenine derivative, e.g., 2,3,3-trimethylindolenine, with an alkenyl halide $R_1$-X, e.g., allyl or hexenyl iodide, extracting the Fischer base obtained with ether and evaporating to dryness the etheral solution.

Figure 1:
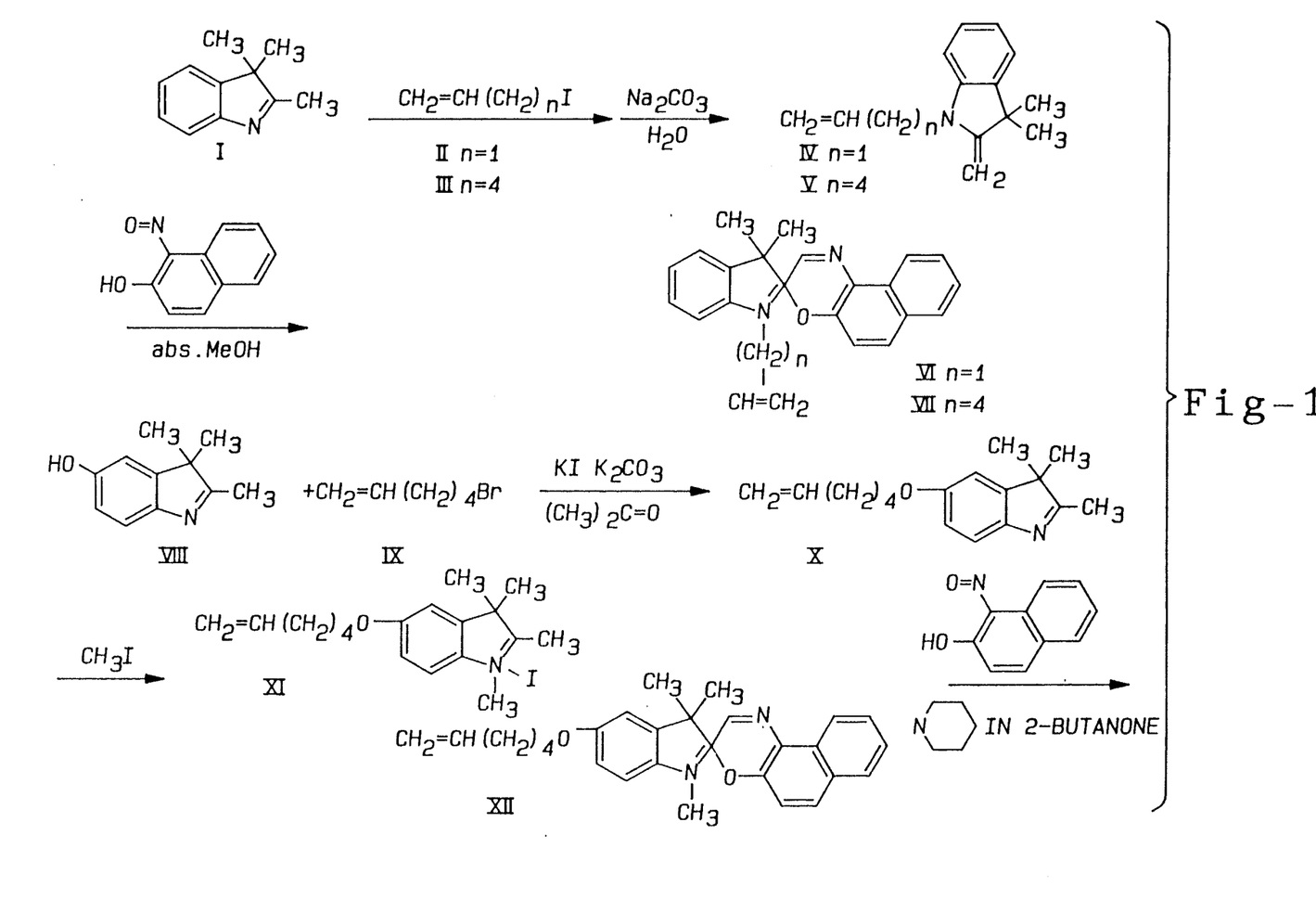
FIG. 1 shows reaction schemes of the synthesis of three photochromes of the present invention.

To form the photochromic compound wherein one of group $R^2$ through $R^7$ includes the linker arm (C) —X(CH$_2$)$_n$—CH=CH$_2$, the linker arm is first introduced into the indole compound by a substitution reaction well known in the art, for example as shown in FIG. 1 for the preparation of the hexenyl ether of 2,3,3-trimethyl-5-hydroxy-indole. Then, the 1-alkyl indolium derivative is formed by reaction with alkyliodide, and is then reacted with the suitable 1-nitroso-2-naphthol or 6-hydroxy-5-nitroso quinoline derivative to produce a monomer of the invention as depicted in FIG. 1B. If, instead of the hydroxy-indole and alkenyl halide starting compounds, indole derivatives having an amino (—NH$_2$ or —NHR'), hydroxy, carboxy or formyl radical are reacted with suitable halides, amines or carboxylic acids, then compounds wherein X is NR' (R' is H or alkyl), CO—O, O—CO, CO—NH, NH—CO, or —CH=N are obtained.

In the photochromic compound, the benzene or pyridine ring formed by $R^9$ and $R^{10}$ can be optionally substituted by lower alkyl, halogen, —CF$_3$, or lower alkoxy groups. By lower alkyl, C$_1$ through C$_6$ alkyl moieties are preferred.

Again, other substitutions at the various groups not substituted by the linker arm can be accomplished by addition or substitution reactions well known in the art once the present invention is understood. The Crano et al. reference[1] cited above exemplifies such modifications to spirooxazine compounds.

The photochromic monomers of the present invention can be used to form novel photochromic polysiloxanes including functional moieties selected from the groups consisting of

(D)

and one or both of the functional moiety selected from the group including (E)

and

-continued (F)

wherein R" is a $C_1$ through $C_{15}$ alkyl, R''' is H or $C_4$ through $C_{15}$ alkyl, G is a photochromic radical derived from a compound as defined above covalently bonded through the alkene carbon of radical $R^1$ as moiety (B) or of $R^2$ through $R^8$ as moiety (C); and the polysiloxanes being cyclic or linear including terminal groups of the formulas:

(R")$_3$—Si—O—, covalently bonded to the Si atom of an (Si—O) moiety and Si—[R"]$_3$ covalently bonded to the —O— atom of an [Si-O] moiety.

By the aforementioned definition of the invention, a linear polysiloxane can be formed having the formula wherein k is an integer of at least 30, x and 1 are integers, the sum of x and 1 are less than k, one of x and 1 can be equal to zero, and n is an integer of 1 through 20.

Alternatively, a cyclic polysiloxane can be formed having the formula wherein m is an integer of at least 4, n is an integer of 1 through 20 and y is an integer less than m.

The values of k and m are inherent properties derived from commercially available siloxane polymers. Hence, since the values of k and m are not at all rate limiting on the synthetic reactions of the invention and there is no relative limit on the values of k and m as conventional siloxane polymers are derived, the only limitation is their lower value and that they are integers.

The invention further relates to a one-step method for the preparation of photochromic polysiloxane polymers containing spironaphthooxazine photochromic groups connected to the main chain through a flexible alkyl linker arm, which comprises adding a photochromic spironaphthooxazine monomer including an alkene terminated side-chain to an Si-H-containing polymer, wherein the photochromic spironaphthooxazine groups will bind covalently through the alkene carbon to [SiH] moieties of the siloxane polymer. The reaction is preferably carried out in the presence of a metal catalyst, most preferably Pt catalyst.

Unlike the prior art two-step substitution reactions or the solute/solvent relationship of photochromic compound to siloxane polymer, the present invention provides a one-step addition reaction wherein an alkene moiety of the photochromic compound reacts with the [Si—H] moiety of the polymer to form a covalent bond of the photochromic compound through a spacer to the backbone of either a cyclic or linear siloxane polymer to form the photochromic polysiloxane polymer. As shown in the experimental section, this reaction can proceed in the presence of platinum catalyst to a high degree of completion of about 100% substitution.

An advantage of the polysiloxanes of the present invention as compared to the prior art[6] is that they do not include free acid moieties which can influence the photochromic reaction kinetics by reacting with already incorporated spirooxazine moieties in a way that causes damage to the photochromic properties. Further, polymers of the present invention can include a one-to-one ratio of Si—O to photochromic compound, thus increasing the optical density to maximal values. They also provide excellent control of color density because as stated above, the rate of coloring and decoloring are also controllable by selection of the length (amount of carbons) of the linker arm.

As a rule, both photochemical and thermal reactions are retarded by polymeric matrices, as compared with liquid. The effect is usually attributed to the steric hindrance of the reactions by the polymeric medium. Such hindrance is particularly pronounced when the photochemical and thermal reaction involves a significant conformational change of the molecule. In the case of photochromic polymers additional factors such as very close vicinity or aggregation of photochromic groups, may play a significant role. The present invention overcomes these problems.

The size of the linker arm may be preferentially determined by proper selection of a spacer component from amongst the substituents $R^1$ through $R^8$. Compounds can be specifically tailored and custom designed to enable the addition of a photochromic group practically to each recurring unit of the polymer backbone resulting in polymers in which the photochrome mol fraction is nearly 100%.

It has been further found that the novel photochromic polymers made in accordance with the present invention have good mechanical strength and scratch resistance. Because of the nearly 100% photochrome mol fraction of those polymers, even thin layers and films of these materials can be effective in attenuating light.

Critical to the aforementioned monomers and compounds is the ability to use the novel monomers to form the photochromic polysiloxanes in a single-step reaction. That is, the photochromic polysiloxanes are made by first forming a photochromic spironaphthooxazine monomer including an alkene-terminated side chain, and, by addition reaction, covalently bonding the alkene carbon to —SiH— moieties of the siloxane polymer in a single-step reaction. In other words, unlike prior art reactions which required first an initial modification of the polymer followed by a substitution reaction, the present invention provides a single-step addition reaction utilizing the alkene linker arms of the novel photochromic compounds of the present invention. More specifically, the spironaphthooxazine monomer as defined above is reacted with either a linear or cyclic polysiloxane at elevated temperature and in the presence of platinum catalyst. The yields of polymers in accordance with the present inventive method can range from about 50% for some cyclic polymers to 90% for linear polymers.

EXPERIMENTAL SECTION

The invention will now be illustrated by the following examples to which it is not limited. In these examples the following chemicals were used without further purification: 2,3,3-trimethyl-indoline (Aldrich), allyl iodide (BDH), 6-bromo-1-hexene (Fluka), 1-nitroso-2-naphthol, 98 (Aldrich). Polymers used are poly(methylhydrosiloxane), n=35 (Merck), tetra(methylhydrosiloxane) and penta(methylhydrosiloxane) (Petrarch Systems).

Optical absorption measurements were performed on a Varian 2200 spectrophotometer with a heating-cooling attachment. For some polysiloxane films, the spectra were taken at low temperatures. Flash photolysis was conducted as described[8], using a thin (about 1 μm) polysiloxane film placed at 45° toward the flash lamp. IR spectroscopy was recorded using an FTIR Niolet-50 spectrometer on thin films supported on NaCl plates.

The content of the photochromic groups in the polysiloxanes (expressed as photochrome mol fraction) was evaluated by elemental analysis (according to the nitrogen content) or by UV-spectroscopy as descibed[11].

EXAMPLE 1

Preparation of
1'-(1-prop-2-enyl)-3',3'-dimethylspiro[indoline-2,3'-[3H]-naphtho[2,1-b]-1,4-oxazine]. (See Compound VII in FIG. 1A)

1a. Synthesis of 1(1-prop-2-enyl)-3,3-dimethyl-2-methylene-indoline (Compound IV in FIG. 1A): A mixture of 2,3,3-trimethyl-indolenine (10 ml) and allyl iodide (6.07 ml, 67 mmol) was heated at 100° C. for 3.5 hours. The solid obtained was dissolved in a mixture of water and ethyl acetate and then basified with sodium carbonate to pH 8. The Fischer base obtained was extracted with ether three times, dried over anhydrous sodium sulfate and passed through a 5 cm column of basic alumina. The etheral solution was evaporated to dryness. The product was reacted without further purification. Yield: 9.5 g (76%).

1b. Synthesis of 1'(1'-prop-2-enyl)-3',3'-dimethyl-spiro(indoline-2,3'-[3H]-naphtho[2,1-b]-1,4-oxazine]: A solution of the Fischer base (Compound IV in FIG. 1A) (9.5 g, 0.047 mol) and 1-nitroso-2-naphthol (8.26 g, 0.047 mol) in 30 ml of methanol was refluxed for 40 minutes. The solvent was evaporated, then the crude material was flash chromatographed on silica gel using ethyl acetate/hexane (1:20) as eluent.

Yield: 4.2 g, (26%). Anal. Calcd. for $C_{24}H_{22}N_2O$: C, 81.96;H, 6.01; N, 7.65. Found: C, 80.84;H, 6.20; N, 7.82.

$^1H$ NMR (CDCl$_3$) δ=1.34 (s, 3H); 1.37 (s, 3H); 3.78 (m, 2H); 5.16 (m, 2H); 5.90 (m, 1H); 6.60 (d, 1H); 6.86–7.80 (9H, aromatic rings); 8.55(d, 1 H, aromatic ring).

EXAMPLE 2

Preparation of
1'(1-hex-5-enyl)-3',3'-dimethylspiro[indoline-2,3'-[3H]-naphtho[2,1-b]-1,4-oxazine]. (Compound VII in FIG. 1A)

2a. 1-(1-hex-5-enyl)-3,3-dimethyl-2-methyleneindoline: A mixture of 2,3,3-trimethyl-indoline (5.5 ml 37 mmol) and 6-iodo-1-hexene (78 g, 37 mmol) was heated at 100° for 3.5 hours. The solid obtained was dissolved in a mixture of water and ethyl acetate and then basified with sodium carbonate to pH 8. The Fischer base obtained (Compound V in FIG. 1A) was extracted with ether three times, dried over anhydrous sodium sulfate and passed through a 5 cm column of basic alumina. The etheral solution was evaporated to dryness and reacted without further purification. Yield: 6.06 g (68%).

2b. 1'-(1-hex-5-enyl)-3',3'-dimethylspiro[indoline-2,3'-[3H]-naphtho-[2, 1-b]-1,4-oxazine]: A solution of Fischer base (Compound V in FIG. 1A) (9 g, 0.037 mol) and 1-nitroso-2-naphthol (6.4 g, 0.034 mol) in 30 ml methanol was refluxed for 40 minutes. The solvent was evaporated and the crude material flash chromatographed on silica using hexane as eluent.

Yield: 3.5 g (24%). Anal. Calcd. for $C_{27}H_{28}N_2O$: C, 81.78;H, 7.12; N, 7.06. Found: C, 81.46;H, 7.13; N, 7.03.

$^1H$ NMR (CDCl$_3$) δ=1.33 (s, 3H); 1.34 (s, 3H); 1.58 (m, 4H); 2.00 (m, 2H); 3.18 (t, 2H); 4.90 (m, 2H); 5.78 (m, 1H); 6.60 (d, 1H); 6.85–7.80 (m, 9H, aromatic rings); 8.55 (d, 1H, aromatic ring).

EXAMPLE 3

Preparation of
5'(1-hex-5-enoxy)-1',3'3'-trimethyl-spiro[indoline-2,3'-[3H]-naphtho[b 2,1-b]-1,4-oxazine](XII) (See FIG. 1B)

3a. 5-(1-hex-5-enoxy)-1,2,3,3-tetramethyl-3H-indolium iodide (XI): mixture of 2,3,3-trimethyl-5-hydroxy indoline (VIII) (3.6 g, 0.02 mol), 6-bromo-1-hexene (X) (2.67 ml, 0.02 mol), potassium iodide (332 g, 0.02 mol) and potassium carbonate (2.76 g, 0.02 mol) was refluxed in dry acetone together with a few drops of dry dimethyl fomamide for 48 hours. The mixture was filtered and the filtrate was evaporated. The crude material was flash chromatographed on silica using ethyl acetate/hexane (1:3) as eluent.

The material obtained (X) was methylated by an overnight reaction with excess methyliodide. The solid obtained was washed with ether and dried to give a clean material, which was found to be of single spot purity by TLC on silica. The eluent used was ethyl acetate/hexane (1:2).

Yield: 31 g (40%).

$^1H$ NMR (DMSO/TMS) δ=1.51 (s, 3H); 2.71 (s, 3H); 3.93 (s,3H); 4.91–5.13 (m, 2H); 5.7 (m, 1H); 7.05–7.85 (aromatic protons).

3b. 5'(1-hen-5-enoxy)-1',3',3-trimethyl-spiro[indoline-2,3'-[3H]-naphtho[2, 1-1,4-oxazine] (XII): A mixture of salt (XI) (3.1 g, 0.0078 mol), 1-nitrosonaphtol (1.34 g, 7.8 mmol) and piperidine in 30 ml 2-butanone (0.77 ml, 7.8 mmol) was refluxed for 1 hour. The solvent was evaporated and the crude product flash chromatographed on silica using hexane/ethyl acetate (20:1) as eluent. Yield: 500 mg (15%).

Anal. Calcd. for $C_{38}H_{30}N_2O_2$; C, 78.84;H, 7.08; N, 6.56.

Found: C, 78.63; H, 6.85; N, 6.66.

$^1H$ NMR (CDCl$_3$) δ=1.33 (s, 3H); 1.36 (s, 3H); 1.58 (m, 4H); 2.15 (m, 2H); 2.70 (s, 3H); 3.95 (t, 2H); 5.00 (m, 1H); 6.45 (d, 1H); 6.70–7.80 (8H, aromatic rings); 8.50 (d, 1H, aromatic ring).

EXAMPLE 4

Preparation of Photochromic Linear Polysiloxanes 750 mg (1.88 mmol) of the spironaphthoxazine derivative (Compound VI) prepared according to Example 1 and 119 mg (1.88 mmol) of linear poly(methylhydrosiloxane), n=35 (Merck) were dissolved in 10 ml of dry toluene. The solution was refluxed for one hour with the condensed solvent being passed through $CaH_2$. The reaction was carried out at room temperature while bubbling through the solution dry nitrogen. Then the catalyst solution of 0.3 mg of $Pt(C_{10}H_{12})Cl_2$ in 1 ml of dry toluene was added. The flask was sealed and kept for at least 36 hours at 80° C. until the Si-H absorption band at 2140 cm$^{-1}$ had totally disappeared. The polymer was redissolved in toluene, re-precipitated from methanol and this procedure was repeated twice. The precipitated polymer was freeze-dried from benzene under high vacuum.

Yield: 64%.

The same procedure was also applied for the preparation of a photochromic linear polysiloxane containing the naphthospiroxazine (Compound VII) prepared according to Example 2.

Polymer films of about 1 μm to 4 μm thickness were prepared from the above polymer by dip-coating a 20% polymer solution in tetrahydrofuran (THF) on a glass slide.

EXAMPLE 5

Preparation of Photochromic Cyclic Polysiloxanes

The same procedure of Example 4 was applied for the synthesis of photochromic cyclic polysiloxanes. 93.2 mg (1.88 mmol) of tetra or penta (methylhydrosiloxane) and 750 mg (1.88 mmol) of the spironaphthooxazine prepared according to Example 1 were dissolved in 10 ml dry toluene. All other steps were the same as in Example 4.

Yield: 57%.

The same procedure was also applied for the preparation of photochromic cyclic polysiloxane containing the spironaphthooxazine prepared according to Example 2.

Films of about 1 μm to 4 μm thickness were prepared from the above polymers by dip coating a 20% polymer solution in THF on a glass slide.

EXAMPLE 6

Kinetics of the Addition of Spirooxazine to Linear Polysiloxane

Figure 2:
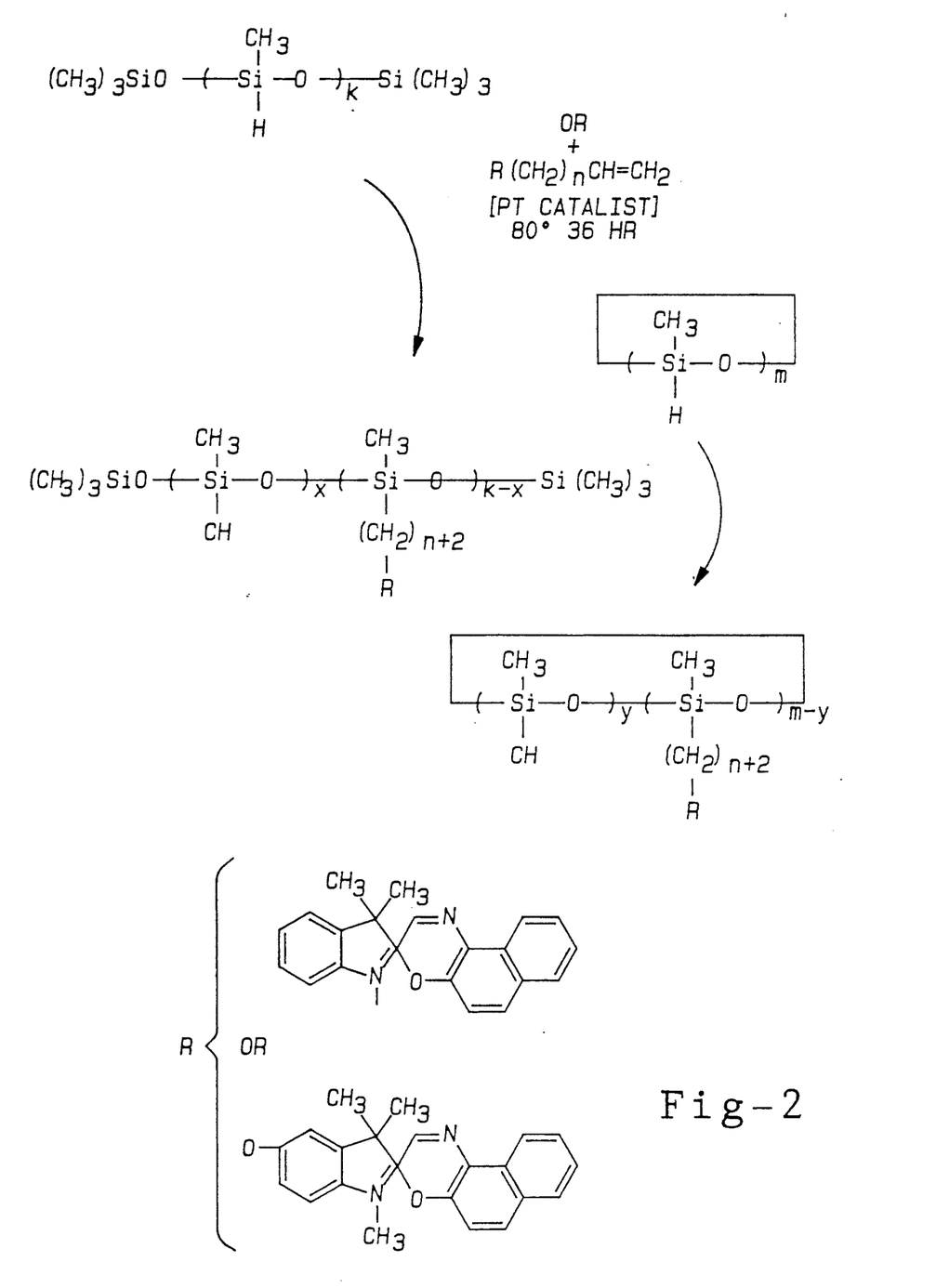
FIG. 2 shows reaction schemes for the synthesis of spironaphthooxazine-containing polysiloxanes of the present invention.
Figures 3, 4:
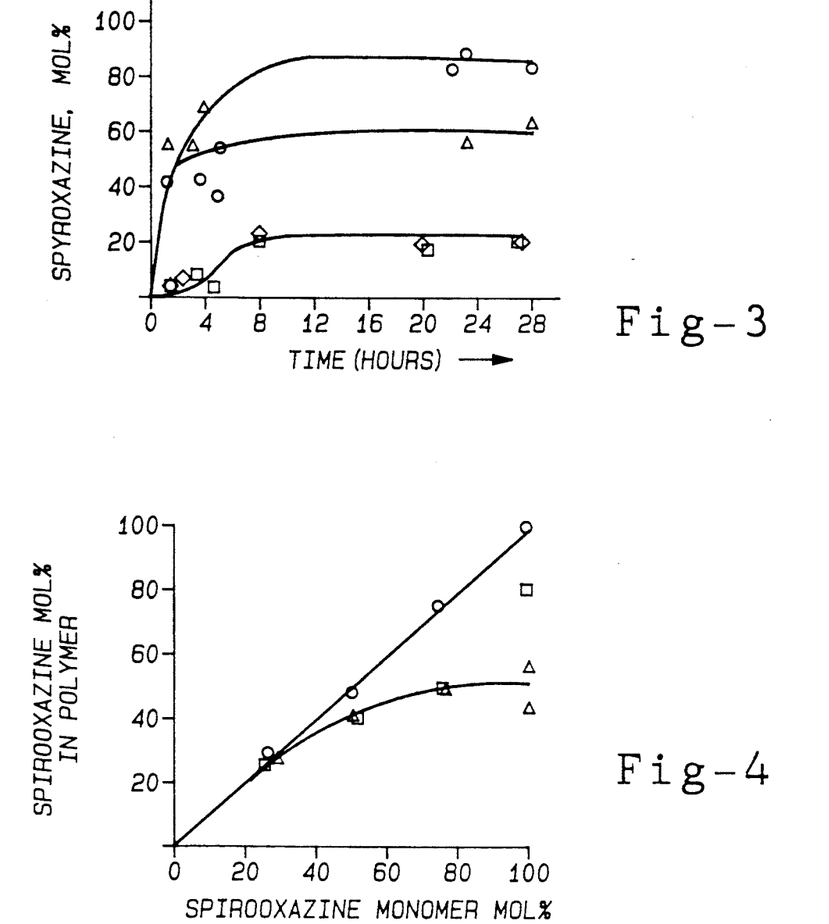
FIG. 3 shows the content of spirooxazine incorporated in the linear polysiloxane as a function of the reaction time: 1, photochromes VI (●) and VII (□) (See FIG. 1), starting photochrome/Si-H ratio in the feed 25 mol %; 2, spirooxazine VI (Δ), starting ratio 100%, 3, spirooxazine VII (○), starting ratio 100%.
FIG. 4 shows content of spirooxazine in the polysiloxanes as a function of the spirooxazine monomer/Si-H bond ratio in the feed; 1, spirooxazine VIII incorporated in the liner polymer (●) and in the cyclic polymer, m=4 (□); 2, spirooxazine VI incorporated in the linear polymer (Δ)

The progress of the addition reaction depicted in FIG. 2 was monitored by measuring the ratio of the peaks Si—H (2164 cm$^{-1}$) to Si—CH$_3$ (1272 cm$^{-1}$), which diminished in the course of the reaction. Calibration of the IR spectra against UV spectra polymers enabled us to observe the kinetics of the addition reaction (FIG. 3). The reaction rate was approximately the same for spirooxazines, with either propene or hexene substituents in the 1'-position, when the starting ratio between spirooxazine and polymer was low (up to 25 mol % spirooxazine, relative to the Si—H bonds). At high ratios of the photochromes (up to 100 mol %), reaction with the propene-substituted spirooxazine slowed down earlier than the reaction with the hexene-substituted photochrome. Apparently, addition of the bulky spirooxazine groups, separated from the main chain only by short (CH$_2$)$_3$ spacers, caused steric hindrance to further incorporation of these groups in the polymer, while the photochrome with the long spacer did not produce this effect. The difference between the two spirooxazines was not observed when the photochrome content in the polymer was low (curve 1, FIG. 3), which confirms the steric character of the effect.

EXAMPLE 7

The Incorporation of Photochromic Groups in Linear and Cyclic Polysiloxane as Function of the Percentage of the Photochromic Compound in the Feed FIG. 4 shows the content of spironaphthooxazine expressed as % of photochrome mol fraction in both linear and cyclic polysiloxanes of the present invention as a function of the spironaphthooxazine monomer/Si—H band ratio in the feed. Curve 1 relates to the preparation of linear (●) and cyclic (□) photochromic polysiloxanes with the long spacer —(CH$_2$)$_6$— between the polymer backbone and the photochromic group, and curve 2 relates to linear photochromic polysiloxanes containing the short spacer —(CH$_2$)$_3$—. As shown in curve 1, up to 100 mol % of the photochrome with the long spacer was incorporated in both cyclic and linear polysiloxanes as against only about 50 mol % of the photochrome with the short spacer (curve 2).

An even more pronounced difference of the results with long and short spacers was observed with the cyclic polysiloxanes (HCH$_3$SiO)$_4$ and (HCH$_3$SiO)$_5$: up to 100 mol % of the photochrome with the long spacer was incorporated to both cyclic polysiloxanes, while only traces of the product of both cyclic polysiloxanes with the photochrome with the short spacer were precipitated by methanol (unsubstituted polysiloxane cycles are soluble in methanol). This means that incorporation of even one photochrome group with the short spacer in the cycles encounters some steric obstacles. In any case, it can be concluded that for the photochrome with the short spacer the steric factor controls the addition reaction.

EXAMPLE 8

Spectra and Color Decay Kinetics

Figure 5:
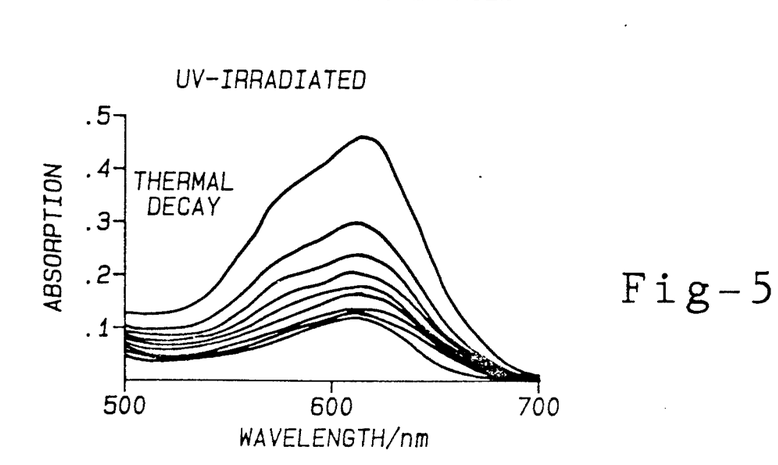
FIG. 5 shows the change of the spectra of a photoactivated photochromic linear polysiloxane film (spirooxazine VI, 70 mol %) during the thermal color decay. The time interval between the upper spectrum and the second spectrum was 2 minutes. Further spectra were recorded after 10 minute intervals.

The absorption spectra resulting from UV irradiation of the photochromic polysiloxanes in the rigid films and in tetrahydrofuran solution are similar (film spectra are given in FIG. 5) and remain unchanged when the temperature or concentration of the photochromic side groups is changed. Similar spectra were reported for photochromic, polymeric, and low molar mass liquid crystals containing spirooxazine units[6,7]. The absorption maximum at 610 nm and a pronounced shoulder around 580 nm indicate two overlapping bands, ascribed to two merocyanine isomers which are in thermal equilibrium with each other. The shape of the spectra remains unchanged during the thermal color decay of the irradiated polymer films (FIG. 5), which is in agreement with the two-isomer assumption. Unlike polymers containing spiropyran photochromic groups[4], there was found no spectral indication of aggregation of merocyanine formed from spirooxazine.

Figure 6A:
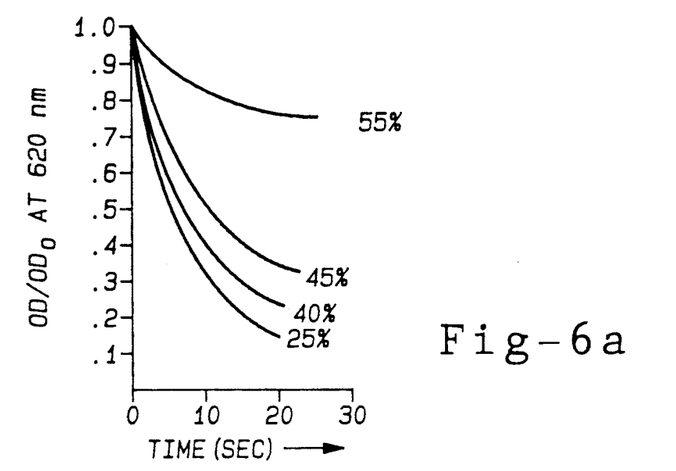
FIG. 6 shows kinetics of the fast color decay measured by flash photolysis at 610 nm for linear polysiloxane polymers with different contents of the photochromes; A,spirooxazine VI; B,spirooxazine VII.
Figure 6B:
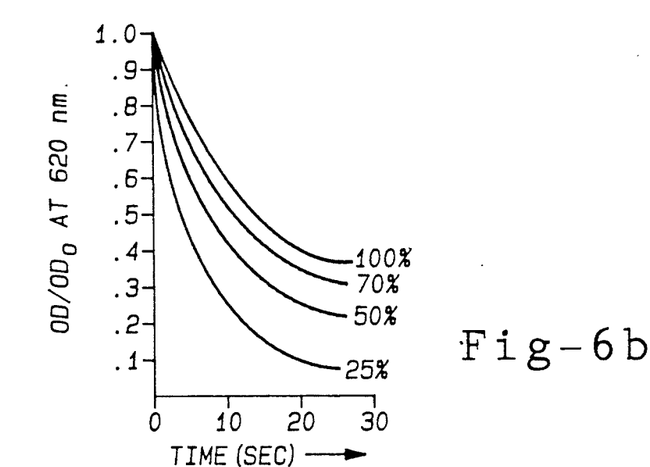
Figure 7A:
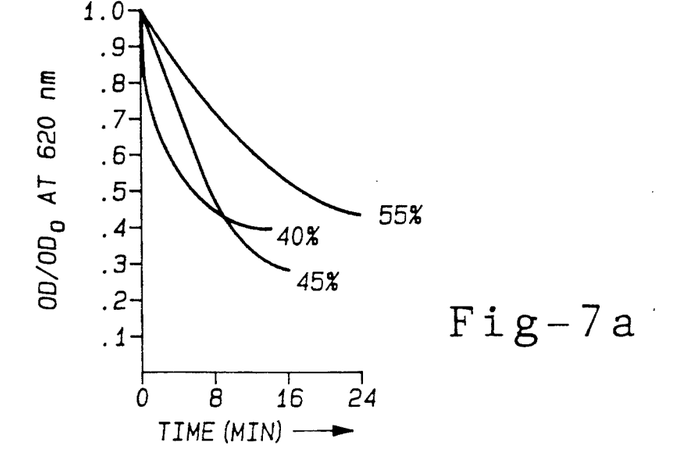
FIG. 7 shows kinetics of the slow color decay for linear polysiloxane polymers with different contents of the photochromes; A,spirooxazine VI; B,spirooxazine VII.
Figure 7B:
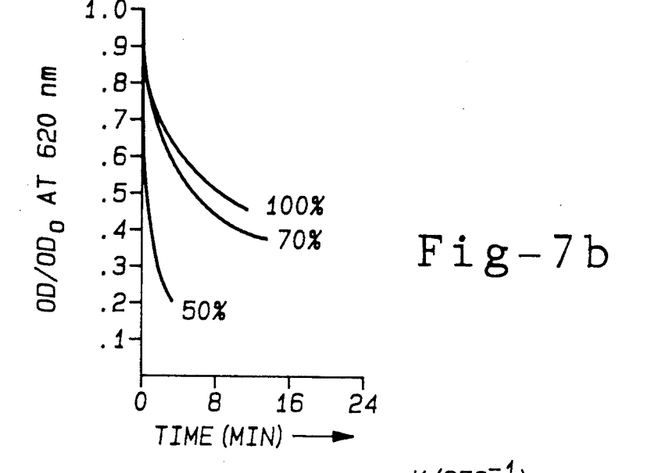

Typical kinetics of decoloration processes of UV-irradiated films are shown in FIGS. 6 and 7. The color decay does not obey first-order kinetics. The initial fast decay (FIG. 6) is followed by a slower decay (FIG. 7). Thus, for example, curve 55% in FIG. 7A is actually a continuation of the same curve in FIG. 6A. It is evident that the fraction of fast initial decay decreases at higher spirooxazine contents, in particular with VI. At 25% spirooxazine content decoloration is practically first order and involves only the fast stage. On the other hand, at the highest spirooxazine content, the second stage of decay is followed by a still slower stage, as may be seen in FIG. 5.

Figures 8, 9:
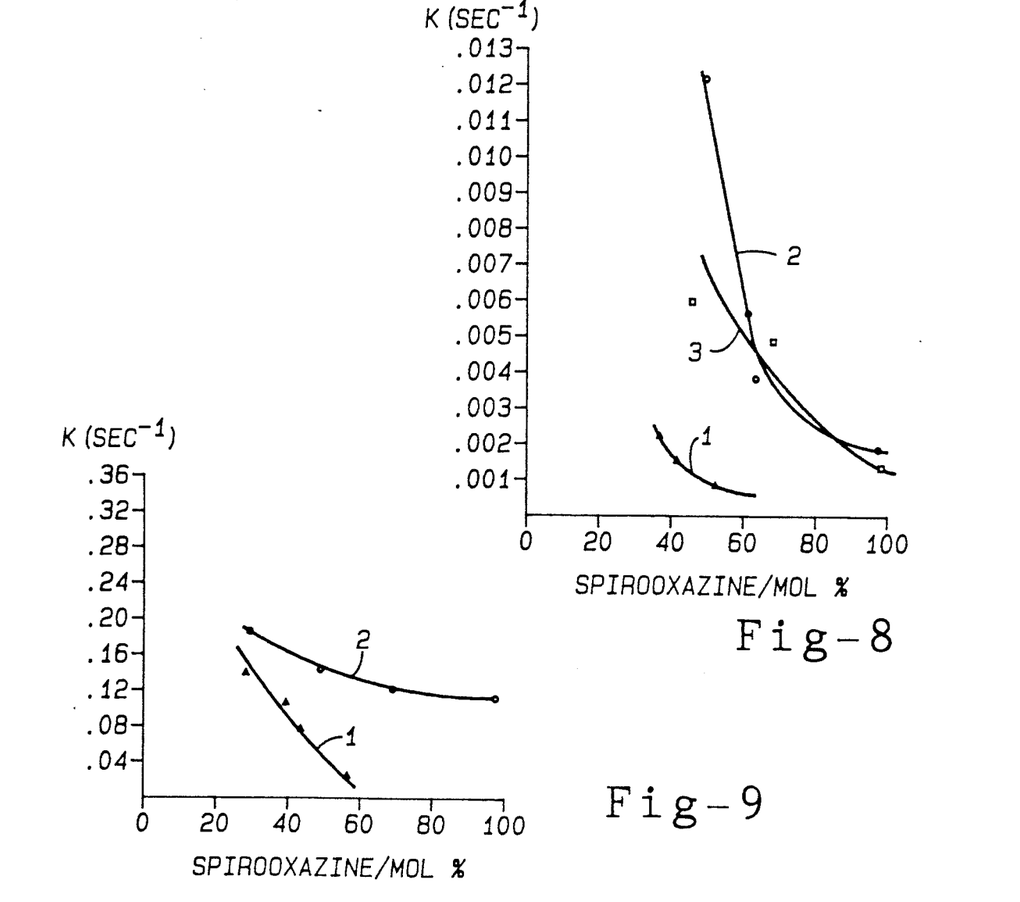
FIG. 8 is a graph showing the dependence of the slow decoloration rate constants on the photochrome content in the linear polymers [1(Δ),spirooxazine VI; 2 (●), spirooxazine VII] and in the cyclic tetrasiloxane [3(□),spirooxazine VII]
FIG. 9 is a graph showing the dependence of the fast decoloration rate constants on the photochrome content in the linear polymers [1(Δ), spirooxazine VI; 2( ),spirooxazine VII].

As a first approximation, the color decay can be described by a sum of two exponential equations, with "fast" and "slow" rate constants[9,10]. For linear polysiloxanes, the rate of the slow and the fast stage decreases with increasing concentration of photochromic groups in the polymer (FIGS. 8 and 9). The slowest decay was observed in the polymer containing the highest possible concentration of spirooxazine groups. In the cyclic polymers containing the photochrome with a long spacer, the color decay occurs practically with the same rate as in the linear polymers (FIG. 8).

Apparently, the deviation from first-order kinetics and the retardation of the color decay at high concentration of the photochromic in polysiloxane stem from the steric hindrance by adjacent bulky photochromic groups. Similar kinetic behavior of acrylic and methacrylic photochromic polymers with spiropyran-merocyanine photochrome proved to be connected with the merocyanine aggregation[9,10].

EXAMPLE 9

Photochromic Polysiloxane Elastomers

Photochromic polysiloxanes containing spirooxazine and hydroxy side groups can be cross-linked by reaction with hexamethylene diisocyanate (HDI). For example, the polymer solution was dissolved in dry toluene and heated to 85° under nitrogen atmosphere. The toluene solution of HDI was added dropwise and stirred. The mixture was heated for an additional three hours to complete the cross-linking reaction.

The reaction can be performed also under milder condition (50° C.) by using dibutyltinoxide as a catalyst.

The coating of the ophthalmic lens surface by the elastomer can be conducted directly from the reaction solution by dipping or spinning with the subsequent washing of the surface with an alcohol-THF mixture and drying of the lens.

EXAMPLE 10

Coating of the Lens Surface with Photochromic Blends

Blends of low molar mass spirooxazine of the present invention and photochromic spirooxazine polysiloxanes were used for coating of ophthalmic lenses by dipping or spinning. The blending of spirooxaxine with a crosslinked spirooxazine polysiloxane polymer was made by swelling of the elastomeric polymer in a spirooxazine solution and subsequent drying of gel.

Example 10 demonstrates the utility of the polymer of the present invention as a lens coating. Such use of the polymers may be by application of the polysiloxanes per se to the substrate lens, or optionally together with stabilizers, such as hindered amine light stabilizer as described by Crano et al.[1].

The invention has been described in an illustrative manner, and it is to be understood that the terminology which has been used is intended to be in the nature of words of description rather than of limitation.

Obviously many modifications and variations of the present invention are possible in light of the above teachings.

What is claimed is:

1. A photochromic polysiloxane including the functional moiety and one or both of the functional moiety selected from the group including and wherein R" is a $C_1$ through $C_{15}$ alkyl, R''' is H or $C_4$ through $C_{15}$ alkyl, G is a photochromic radical derived from a compound wherein said compound is a photochromic compound of the formula:

wherein $R^1$ is selected from the group consisting of (A) hydrogen, alkyl, phenyl, benzyl, or an alkyl substituted by halogen, hydroxy, lower alkoxy, carboxyl, lower alkoxycarbonyl, and phenyl and benzyl substituted by cyano or by one or more halogens; and (B) $(CH_2)_n$—CH=CH$_2$ wherein n is an integer from 1 to 20;
  when $R^1$ is (B), then $R^2$ through $R^8$ are each selected from the group consisting of hydrogen, lower alkyl, and lower alkyl including substitutions from the group consisting of halogen, hydroxy, and lower alkoxy;
  when $R^1$ is (A) then one of $R^2$ through $R^8$ is (C) —X—$(CH_2)_n$—CH=CH$_2$, wherein n is an integer from 1 to 20 and X is selected from the group consisting of a covalent bond, O, N—R', (wherein R' is H or lower alkyl), CO—O, CO—NH, and —CH=N and the remaining ones of $R^2$ through $R^8$ are selected from the group consisting of hydrogen, alkyl, and alkyl substituted by halogen, hydroxy and lower alkoxy; and $R^9$ and $R^{10}$ form a condensed benzene or pyridine ring, covalently bonded through the alkene carbon of radical $R^1$ as moiety (B) or of $R^2$ through $R^8$ as moiety (C); and the polysiloxanes being cyclic or linear including terminal groups of the formulas (R")$_3$—Si—, covalently bonded to the Si atom of an [Si—O] moiety and Si-(R")$_3$ covalently bonded to the —O— atom of an [Si—O] moiety.

2. A polysiloxane of claim 1 of the formula wherein k is an integer of at least 30, x and l are integers, the sum of x and l are less than k, one of x and l can equal 0, n is an integer of 1 through 20 and R", R'" and G are defined as in claim 8.

3. A polysiloxane of claim 2 wherein R" is $CH_3$, k is 35, l is 0, n is 1 or 4 and G is a radical

4. A polysiloxane of claim 1 of the formula wherein m is an integer of at least 4, n is an integer of 1 through 20, y is an integer less than m, and G is as defined in claim 8.

5. A cyclic polysiloxane of claim 4 wherein m is 4 or 5, n is 1 or 4 and G is a radical

6. A method of making a photochromic polysiloxane including the steps of:
  forming a photochromic spironaphthooxazine monomer including an alkene terminated side chain; and
  by, addition reaction, covalently bonding the photochromic spironaphthooxazine monomer through the alkene carbon to [SiH] moieties of a siloxane polymer.

7. A method as set forth in claim 6 wherein said reaction is conducted in the presence of Pt catalyst.

8. A method as set forth in claim 7 further characterized by reacting the siloxane polymer of the formula:

photochromic spironaphthooxazine monomer to form the photochromic polysiloxane of the formula:

wherein k is an integer of at least 30, x and l are integers, the sum of x and l are less than k and one of x and l can equal zero, n is an integer of 1 through 20, R" is a $C_1$ through $C_{15}$ alkyl, R'" is hydrogen and G is a radical derived from a compound wherein said compound is a photochromic compound of the formula:

wherein $R^1$ is selected from the group consisting of (A) hydrogen, alkyl, phenyl, benzyl, or an alkyl substituted by halogen, hydroxy, lower alkoxy, carboxyl, lower alkoxycarbonyl, and phenyl and benzyl substituted by cyano or by one or more halogens; and (B) $(CH_2)_n$—$CH$=$CH_2$ wherein n is an integer from 1 to 20;
  when $R^1$ is (B), then $R^2$ through $R^8$ are each selected from the group consisting of hydrogen, lower alkyl, and lower alkyl including substitutions from the group consisting of halogen, hydroxy, and lower alkoxy;
  when $R^1$ is (A) then one of $R^2$ through $R^8$ is (C) —X—$(CH_2)_n$—$CH$=$CH_2$, wherein n is an integer from 1 to 20 and X is selected from the group consisting of a covalent bond, O, N—R', (wherein R' is H or lower alkyl), CO—O, CO—NH, and —CH=N and the remaining ones of $R^2$ through $R^8$ are selected from the group consisting of hydrogen, alkyl, and alkyl substituted by halogen, hydroxy and lower alkoxy; and $R^9$ and $R^{10}$ form a condensed benzene or pyridine ring.

9. A method as set forth in claim 8 further characterized by reacting the siloxane polymer with the photochromic spironaphthooxazine monomer in the presence of an alkene of $C_4$-$C_{15}$ thus forming a photochromic polysiloxane wherein R'" is hydrogen and $C_4$-$C_{15}$ are alkyl.

10. A method as set forth in claim 8 further characterized by reacting the siloxane polymer of the formula:

with the photochromic spironaphthooxazine monomer as defined in claim 1 to form the photochromic cyclic polysiloxane of the formula:

wherein m is an integer equal to at least 4, n is an integer of 1 through 20; y is an integer less than m and G is as defined in claim 15.

11. A coated article comprising:
 a substrate layer; and
 a coating layer consisting of a polysiloxane as defined in claim 1.

12. A coated lens comprising:
 a lens substrate coated with a polysiloxane as set forth in claim 1.

* * * * *